United States Patent [19]

Fujino et al.

[11] 4,100,152
[45] Jul. 11, 1978

[54] PEPTIDES

[75] Inventors: Masahiko Fujino, Takarazuka; Osamu Nishimura, Toyonaka; Yuji Nagawa, Nagaokakyo; Naohisa Fukuda, Toyonaka, all of Japan

[73] Assignee: Takeda Chemical Industries, Ltd., Osaka, Japan

[21] Appl. No.: 778,321

[22] Filed: Mar. 16, 1977

[30] Foreign Application Priority Data

Mar. 23, 1976 [JP] Japan .................................. 51-32170

[51] Int. Cl.$^2$ ..................... C07C 103/52; A61K 37/00
[52] U.S. Cl. ............................ 260/112.5 TR; 424/177
[58] Field of Search ............... 260/112.5 TR; 548/344

[56] References Cited

U.S. PATENT DOCUMENTS

| 3,753,969 | 5/1973 | Folkers et al. ............ 260/112.5 TR |
| 3,821,188 | 6/1974 | McKinley et al. ................ 260/112.5 |
| 3,959,248 | 5/1976 | Veber et al. ............... 260/112.5 TR |

FOREIGN PATENT DOCUMENTS

| 2,449,167 | 4/1976 | Fed. Rep. of Germany .... 260/112.5 TR |

OTHER PUBLICATIONS

Bowers et al., Biochem. Biophys. Res. Comm., vol. 40, pp. 683–691 (1970).
Chang et al., J. Med. Chem., vol. 14, pp. 484–487, (1971).

Primary Examiner—Delbert R. Phillips
Assistant Examiner—Blondel Hazel
Attorney, Agent, or Firm—Wenderoth, Lind & Ponack

[57] ABSTRACT

A novel peptide of the formula:

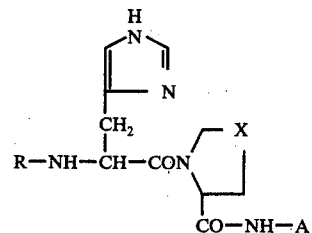

wherein A is hydrogen, alkyl, aralkyl, alkoxyalkyl, hydroxyalkyl or alkoxy; R is

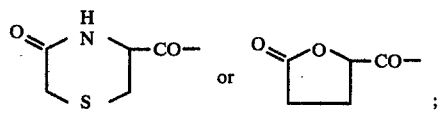

X is —S— or —(CH$_2$)$_n$— where n is 1 or 2 has a weaker TRH releasing activity than TRH and a stronger anaesthesia-antagonistic activity, spontaneous movement-stimulant activity or dopamine-potentiating activity than TRH.

3 Claims, No Drawings

PEPTIDES

This invention relates to novel peptides of the following formula:

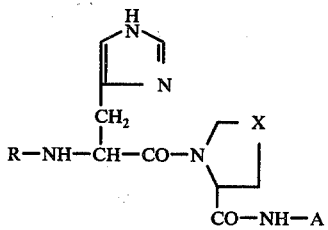

Wherein A is hydrogen, alkyl, aralkyl, alkoxyalkyl, hydroxyalkyl or alkoxy; R is

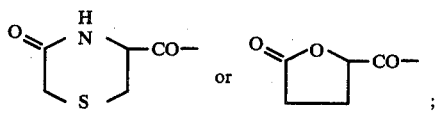

X is —S— or —$(CH_2)_n$— where n is 1 or 2; R and other constituent amino acid residues may each be L- or D-configurated or racemic.

A first object of this invention is to provide novel peptides of the formula (I). Another object is to provide peptides (I) which, whilst being weaker than the known TRH (L-pyroglutamyl-L-histidyl-L-prolinamide) in TSH (thyroid stimulating hormore)-releasing activity, are stronger than said known TRH in at least one of anaesthesia-antagonistic activity, spontaneous movement-stimulant activity and dopamine-potentiating activity.

Referring to the above formula (I), the alkyl group represented by A is preferably a straight-chain or branched alkyl of up to 10 carbon atoms (e.g. methyl, ethyl, propyl, iso-propyl, butyl, sec-butyl, tert-butyl, iso-butyl, amyl, hexyl, octyl, nonyl, decyl, etc.). The aralkyl group represented by A is preferably a group consisting of a phenyl group to which a straight-chain or branched alkylene group of 1 to 4 carbon atoms (e.g. methylene, ethylene, 1,3-trimethylene (—$CH_2CH_2CH_2$—), propylene

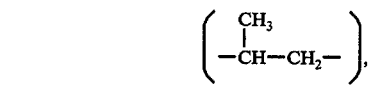

—$CH_2CH_2CH_2CH_2$—,

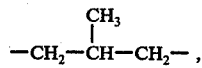

etc.) is attached. The alkoxyalkyl group represented by A is preferably a straight-chain or branched group of up to 9 carbon atoms (e.g. methoxymethyl, methoxyethyl, propoxypropyl, butoxybutyl, methoxyoctyl, etc.). The alkoxy group represented by A preferably contains up to 9 carbon atoms, being exemplified by alkoxy groups corresponding to the alkyl groups A mentioned above.

The hydroxyalkyl preferably contains 1 to 9 carbon atoms. As examples thereof, there may be mentioned the alkyl groups of 1 to 9 carbon atoms as mentioned for A which have been substituted by hydroxyl in any optional position.

Throughout this specification, the amino acids, peptides, compound residues, protective groups, solvents, etc. are sometimes designated by abbreviations according to IUPAC-IUB Commission on Biological Nomenclature or by the trivial names commonly used in the art.

The following is a partial list of those abbreviations and trivial names.

His: histidine
Pro: proline
Pip: pipecolic acid
Glu: glutamic acid
Tac: meta-thiazolidine-5-carboxylic acid

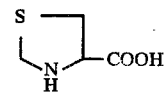

Oct: 3-oxo-5-carboxyperhydro-1,4-thiazine

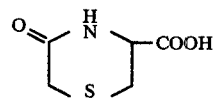

Cbl: γ-carboxy-γ-butyrolactone

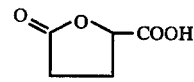

Z: benzyloxycarbonyl
BOC: t-butoxycarbonyl
DCC: dicyclohexylcarbodiimide
$N_3$: azide
O'Bu: t-butylester
Tos: tosyl p1 HONB: N-hydroxy-5-norbornene-2,3-dicarboximide
Hobt: N-hydroxy-1,2,3-benzotriazole
Hosu: N-hydroxysuccinimide
DCHA: dicyclohexylamine
DMF: dimethylformamide The above abbreviations may stand for the residues of the corresponding compounds capable of forming a peptide bond.

The contemplated compounds (I) of this invention may be produced by procedures known for the synthesis of peptides. The introduction of protective groups, the manner of forming peptide linkages, the removal of protective groups, etc. may be conventional per se. The compounds (I) may be produced either in liquid phase or in solid phase. The processes for peptide synthesis per se which may be employed for the production of compounds (I) are described in, for example, The Peptides, Vol. 1 (1966), Schröder and Lubke, Academic Press, New York, U.S.A.; Amino Acids, Peptides and Proteins, Vols. 1–5, ed. by G. T. Young. published from The Chemical Society, London; Peptide Synthesis by Nobuo Izumiya (Maruzen); and U.S. Pat. No. 3,870,694 issued to Fujino et al. Thus, there may be mentioned DCC/HONB process, azide process, chloride process, acid anhydride process, mixed anhydride process, DCC process, activated ester process, the process employing Woodward's Reagent K. carbodiimidazole process, redox process, EEDQ (1-ethoxycarbonyl-2-ethoxy-1,2-dihydroquinoline) process and so forth.

In the production of the contemplated compound (I) of this invention, the starting materials corresponding to the two portions divided by one of the following three dotted lines may be reacted together in a manner conventional per se.

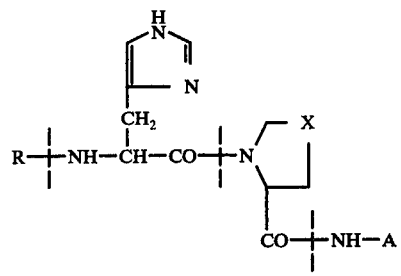

The following are typical examples of the production process.

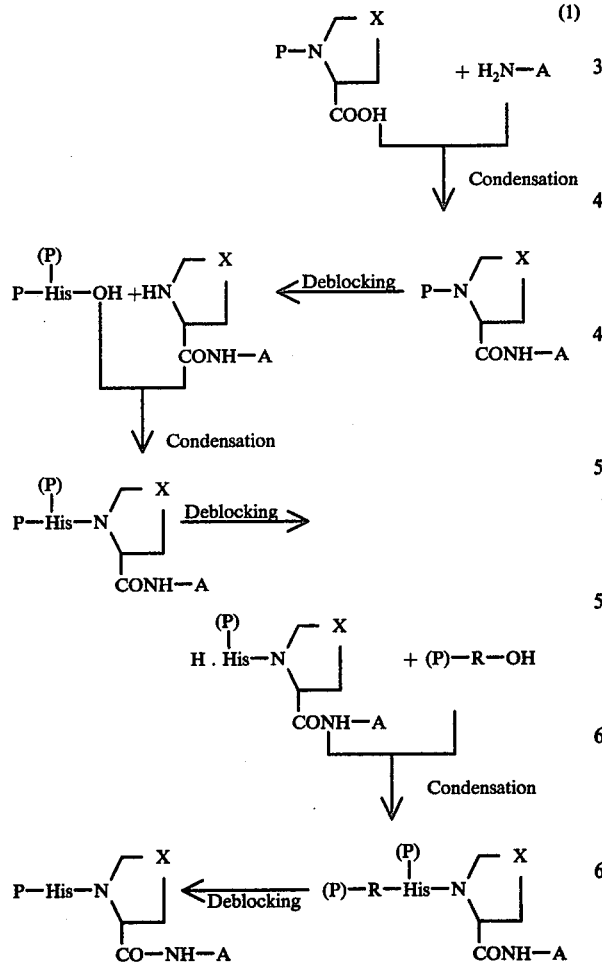

-continued

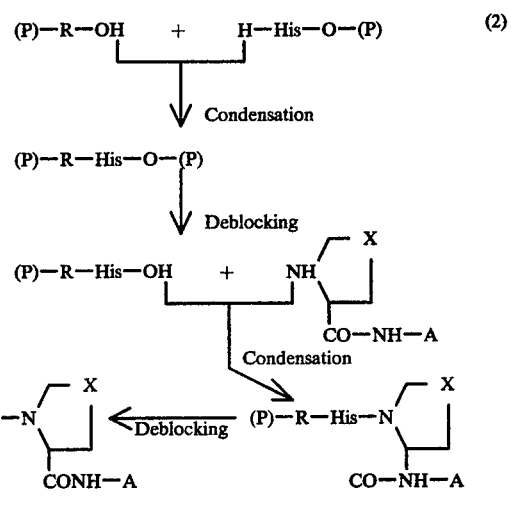

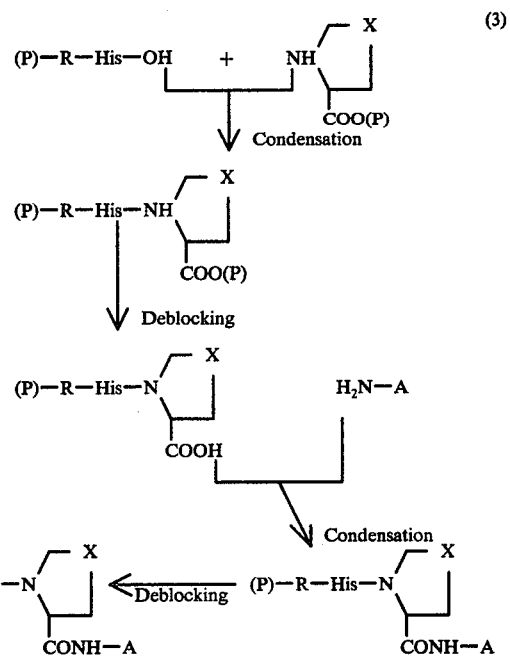

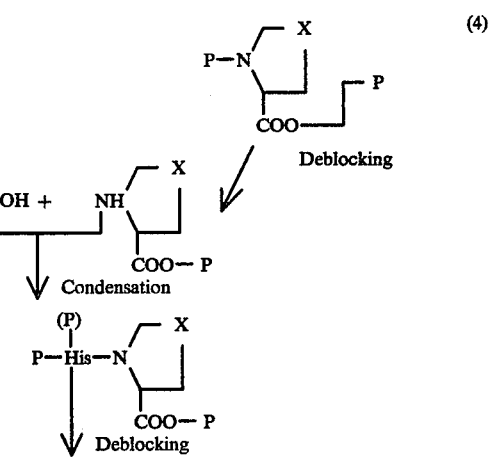

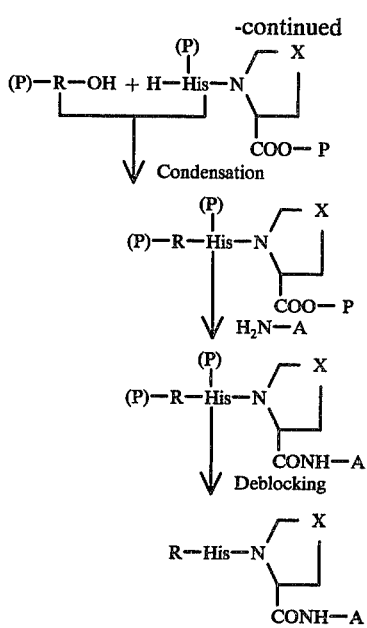

In the above formulas, P is a protective group; (P) means that a protective group is not necessarily required; P is a resin for use in solid-phase synthesis; the term 'condensation' means not only condensation by means of a dehydrative condensing agent but also condensation via an intermediate such as the azide, chloride, activated ester or the like.

Prior to the reaction for the formation of a peptide bond in the production of contemplated compound (I), the functional groups such as amino, imino and carboxyl which will or ought not to be involved in the reaction may be protected with protective groups in the known manner. The amino, imino and carboxyl groups pertinent to the peptide-forming reactions may be activated by known activating procedures.

As the protective groups for the α-amino group of any starting material (e.g. α-amino group of histidine) which does not take part in the reaction, there may be mentioned conventional protective groups such as Z, BOC, t-amyloxycarbonyl, isobornyloxycarbonyl, phthaloyl, trifluoroacetyl, formyl, etc. As the protective group for the imidazole nucleus of the histidine moiety, it may be one of the known groups, such as tosyl, benzyl, 2,4-dinitrophenyl, etc., although such protection may not be essential.

The carboxyl group of the starting compound, which does not take part in the contemplated reaction may be previously protected with a known protective group. Thus, for example, it may be protected in the form of an ester (e.g. methyl, ethyl, benzyl, p-nitrobenzyl, t-butyl or t-amyl ester) or a metal salt (e.g. sodium or potassium salt).

The carboxyl group which will be involved in the contemplated reaction may be previously activated in such known forms as activated esters (pentachlorophenol, 2,4,5-trichlorophenol, 2,4-dinitrophenol, cyanomethyl alcohol, p-nitrophenol, N-hydroxy-5-norbornene-2,3-dicarboximide, N-hydroxysuccinimide, N-hydroxyphthalimide and N-hydroxy-1,2,3-benzotriazole esters) or the carboxylic anhydrides, azides, etc. corresponding to the starting material carboxylic acids. Among the above-mentioned activated esters, N-hydroxy-5-norbornene-2,3-dicarboximide, N-hydroxy-1,2,3-benzotriazole, N-hydroxysuccinimide, etc. are in certain cases more advantageous for the condensation reaction of the histidine moiety because of their relatively reduced tendency toward inducing racemization.

The present condensation reaction may be conducted in a solvent which does not interfere the desired reaction (e.g. DMF, chloroform, dioxane, tetrahydrofuran).

Reaction temperature and time can be selected suitably from the ranges employed in conventional peptide synthesis, and they preferably be from about −30° to about 60° C and from about 2 to about 24 hours.

Where the peptide produced by this condensation process has a protective group, the protective group can be removed by a conventional procedure. As examples of such deblocking procedure may be mentioned catalytic reduction with a catalyst (e.g. palladium black, palladium-on-carbon, platinum, etc.), solvolysis by means of an acid reagent (e.g. hydrogen fluoride, hydrogen bromide, hydrogen chloride, trifluoroacetic acid, etc.) and reduction with sodium in liquid ammonia.

At the end of the reaction, the product compound (I) may be separated from the reaction mixture as the free compound, or in the form of an acid salt, by procedures known per se (e.g. phasic transfer, extraction, chromatography, crystallization, reprecipitation, etc.).

The starting materials for the production of compounds (I) can also be prepared by known procedures or procedures analogous thereto.

The product compounds (I) are able to form salts with pharmacologically acceptable inorganic acids (e.g. hydrochloric acid) or organic acids (e.g. acetic acid, tartaric acid).

The product compounds (I) according to this invention are of value as they display at least one of anaesthesia antagonism, sleep antagonism, spontaneous movement-stimulating activity and dopamine-potentiating activity in animals (e.g. mouse, rat, cat, dog, monkey). Furthermore, since these compounds have no or little TSH-releasing activity, they are of value in this respect as well. Of the compound (I), the L-isomer is most desirable and the racemic mixture is second. Compounds (I) may be administered to animals (e.g. mouse, rat, cat, dog, monkey) or to human beings as palinesthesias, spontaneous movement stimulants or dopamine-potentiators.

Compounds (I) are also useful in the treatment of hypnotic intoxication, clouding of conciousness, hyperkinesia, schizophrenia, depression and parkinsonism.

The possible routes of administration are by parenteral (e.g. intravenous, intramuscular, subcutaneous), oral, reactal, nasal and other routes.

The dosage of compound (I) necessary to attain the above-mentioned effects depends upon the particular species of compound (I), the species and health of animal, route of administration, etc. For example, one may select an appropriate dose from the range of about 0.1 mg/kg to 10 mg/kg (per dose) in the case of parenteral administration and from the range of about 5 mg/kg to 500 mg/kg (per dose) for oral use.

While compounds (I) may be administered as they are, they may be formulated into dosage forms similar to those of known TRH(e.g. injectable preparations, powders, tablets).

In all the examples and pharmacological test data given hereinafter, all references to amino acids, peptides and other compounds involving optical isomers are made to L-compounds unless otherwise indicated.

EXAMPLE 1

Synthesis of Oct.His.Pro.NH$_2$ (a) Synthesis of 3-oxo-5-carboxyperhydro-1,4-thiazine In 40 ml. of water is suspended 3.6 g (0.02 M) of S-carboxymethyl-L-cysteine, followed by addition of 20 ml. of 1N-NaOH. The reaction is conducted in a sealed tubular reactor at 110° C for 48 hours. The reaction mixture is passed through a column (4.5 × 12.0 cm) of Amberlite IR-120 B (H$^+$-form), whereby it is desalted. The effluent is concentrated to dryness and the residue is dissolved in glacial acetic acid. Following addition of ether, the resultant crystals are recovered by filtration. Yield 1.55 g. (48.1%); melting point: 152.0°–153.0° C; optical rotation $[\alpha]_D^{25} + 1.1°$ (c=0.64, in water).

Elemental analysis, for C$_5$H$_7$O$_3$NS - Calcd. C, 37.26; H, 4.38; N, 8.69; S, 19.89; Found. C, 36.97; H, 4.28; N, 8.54; S, 19.73.

(b) Synthesis of Z-His-Pro-NH$_2$

With palladium black as the catalyst, 32.7 g (0.12 M) of Z-Pro-NH$_2$ is catalytically reduced in methanol in the conventional manner. The catalyst is filtered off and the filtrate is concentrated under reduced pressure. The resultant crystalline residue is dried well in vacuo. Separately, 36.4 g. (0.12 M) of Z-His-NH.NH$_2$ is dissolved in 360 ml. of 1N-HCl and, after 480 ml. of ethyl acetate is added, the solution is cooled to 0° C. With vigorous stirring, an aqueous solution (30 ml.) of 8.3 g.(0.12 M) of sodium nitrite is added dropwise. After 3 minutes, 144 ml. of a cold 50% solution of potassium carbonate is added. The ethyl acetate layer is taken and the water layer is extracted with ethyl acetate. Both extracts are pooled and dried over anhydrous Na$_2$SO$_4$. This dried ethyl acetate solution is combined with the dry powder previously obtained, followed by vigorous stirring. To this reaction mixture is added 150 ml. of N,N-dimethylformamide and the mixture is stirred at 4° C for 12 hours, at the end of which time the solvent is distilled off. The oily residue is crystallized by addition of cold water. It is further recrystallized from water. Yield 24.5 g. (53.0%); melting point: 112.0°–118.0° C; optical rotation $[\alpha]_D^{22} - 39.8°$ (c=0.53, in water).

Elemental analysis, for C$_{19}$H$_{23}$N$_5$O$_4$.1/2H$_2$O - Calcd. C, 57.86; H, 6.13; N, 17.76; Found C, 58.16; H, 6.03; N, 17.65.

(c) Synthesis of Oct.His.Pro.NH$_2$

In 15 ml of 25% HBr/acetic acid is dissolved 1.20 g (0.00312 M) of Z.His.Pro.NH$_2$ and the solution is allowed to stand at room temperature for 40 minutes. Following addition of 150 ml. of ether, the resultant precipitate is recovered by filtration and dried in a desiccator with NaOH for 12 hours. The dried powder is dissolved in 20 ml. of N,N-dimethylformamide and, under cooling, 0.88 ml. (0.00624 M) of triethylamine is added. The resultant salt crystals are removed, and 502 mg. (0.00312 M) of 3-oxo-5-carboxyperhydro-1,4-thiazine and 670 mg. (0.00374 M) of HONB are dissolved in the filtrate. Then, at 0° C, 772 mg. (0.00374 M) of DCC is added, followed by stirring in a refrigerator for 48 hours. The resultant byproduct dicyclohexylurea is filtered off and the filtrate is concentrated in vacuo. To the oily product thus obtained is added ethyl acetate and the resultant precipitate is dissolved in a 70 ml. of solvent mixture of methanol and chloroform (1:9). The solution is run onto a column (4.5 × 6.0 cm) of silica gel and, following the passage of 300 ml. of the same solvent as above, elution is carried out with a mixture of methanol and chloroform (4:6). The fractions rich in the desired product are pooled and, after removal of the solvent by distillation, the oily residue is dissolved in water. The insolubles are filtered off and the filtrate is freeze-dried. Yield 771 mg.; optical rotation $[\alpha]_D^{25} - 57.5°$ (c=0.53, in water); thin-layer chromatography: Rf$_1$(n-butanol-ethylacetate-acetic acid-water = 1:1:1:1, support = silica gel, Pauly's color reaction) 0.34.

Elemental analysis, for C$_{16}$H$_{22}$O$_4$N$_6$S.5H$_2$O - Calcd. C, 39.67; H, 6.65; N, 17.36; S, 6.62; Found C, 39.39; H, 5.12; N, 17.43; S, 6.79.

EXAMPLE 2

Synthesis of Oct.His.Pip.NH$_2$ (a) Synthesis of Z-Pip.NH$_2$

In 50 ml. of a mixture of dioxane and ethyl acetate (4:1) is dissolved 3.95 g. (0.015 M) of Z-Pip.OH and 2.70 g. (0.015 M) of HONB. Then, at 0° C, 3.09 g. (0.015 M) of DCC is added. The mixture is stirred at room temperature for 5 hours. The byproduct dicyclohexylurea is filtered off and 5 ml. of concentrated aqueous ammonia is added dropwise to the filtrate with vigorous stirring. After 5 hours, the solvent is distilled off under reduced pressure and the residue is dissolved in ethyl acetate. The ethyl acetate layer is washed with 5% NaHCO$_3$ and 1N-HCl, followed by drying. The ethyl acetate is distilled off and the residue is crystallized by addition of petroleum benzin. The product is further recrystallized from ethyl acetate-petroleum benzin. Yield 2.62 g. (66.7%); melting point: 110.0°–111.0° C; optical rotation $[\alpha]_D^{26} - 36.1°$ (c=0.42, in methanol).

Elemental analysis, for C$_{14}$H$_{18}$O$_3$N$_2$ - Calcd. C, 64.10; H, 6.92; N, 10.68; Found C, 64.11; H, 6.90; N, 10.67.

(b) Synthesis of Z-His-Pip.NH$_2$

In a routine manner 5.3 g. (0.02 M) of Z-Pip.NH$_2$ is catalytically reduced to H.Pip.NH$_2$. Separately, 6.1 g. (0.02 M) of Z.His.NH.NH$_2$ is converted to the azide as in Example 1(b) and reacted with a solution of H.Pip.NH$_2$ in 100 ml. of DMF at 4° C for 4 days and at room temperature for 24 hours. The solvent is distilled off and the residue is dissolved in a solvent mixture of Rf$_2$ (ethyl acetate-pyridine-acetic acid-water = 60:20:6:11) and purified by chromatography on silica gel (column: 3.0 × 20.0 cm) with the same solvent system as above. The fractions rich in the desired product are pooled and concentrated to obtain an oily product. Yield 4.0 g. (50.0%); optical rotation $[\alpha]_D^{21} - 48.6°$ (c=0.54, in DMF).

Elemental analysis, for C$_{20}$H$_{25}$O$_4$N$_5$.H$_2$O - Calcd. C, 57.54; H, 6.52; N, 16.78; Found C, 57.47; H, 6.48; N, 15.46.

(c) Synthesis of Oct-His-Pip.NH$_2$ 1.20 g. (0.003 M) of oily Z.His-Pip.NH$_2$ is treated with 12 ml. of 25% HBr/acetic acid for 110 minutes, at the end of which time 100 ml. of ether is added. The resultant precipitate is recovered by filtration and dried in a desiccator with NaOH for 12 hours. The dried powder is dissolved in 15 ml. of N,N-dimethylformamide and the solution is neutralized with 0.84 ml. (0.006 M) of triethylamine under cooling. The precipitated salt is filtered off and the filtrate is directly used as the amine component for the next reaction. Meanwhile, 484 mg. (0.003 M) of 3-oxo-5-carboxyperhydro-1,4-thiazine and 540 mg. (0.003 M) of HONB are dissolved in 5 ml. of N,N-dimethylformamide and, under ice-cooling, 618 mg. (0.003 M) of DCC is added. The mixture is stirred for 3 hours. This activated ester solution is combined with the amine component solution prepared above and the entire mixture is stirred at 4° C for 12 hours. The byproduct dicyclohexylurea is filtered off and the filtrate is concentrated in vacuo. The oily residue is triturated with ether. The powder thus obtained is dissolved in 100 ml. of a mixture of methanol and chloroform (1:9) and passed through a column (2.5 × 16.0 cm) of silica gel. The column is first washed with 700 ml. of the same solvent as above and eluted with a mixture of methanol and chloroform 4:6. The fractions rich in the desired compound are pooled and concentrated under reduced pressure to remove the solvent. The residue is dissolved in a small amount of 0.1N-acetic acid and further purified by means of a column (5.5 × 40.0 cm) of Sephadex LH-20. The fractions rich in the compound are pooled and freezedried. Yield 740 mg; optical rotation $[\alpha]_D^{21} - 52.3°$ (c=0.70, in water); thin-layer chromatography $Rf_1 = 0.50$.

Elemental analysis, for $C_{17}H_{24}O_4N_6S \cdot CH_3COOH \cdot 4H_2O$ - Calcd. C, 42.21; H, 6.71; N, 15.55; S, 5.93; Found C, 41.94; H, 5.38; N, 16.00; S, 6.48. Amino acid analysis (hydrolyzed in 6N-HCl at 110° C for 24 hours): His, 0.93(1); s-carboxymethylcysteine, 1.03(1); Pip, 1.00(1), average recovery 94.2%.

EXAMPLE 3

Synthesis of Oct-His-Pro.NH.CH$_3$ (a) Synthesis of Z.Pro.NH.CH$_3$

In 100 ml. of dioxane is dissolved 12.5 g. (0.05 M) of Z.Pro.OH together with 9.8 g. (0.055 M) of HONB and, under cooling, 11.3 g. (0.055 M) of DCC is added. The mixture is stirred at room temperature for 3 hours and the byproduct dicyclohexylurea is filtered off. The filtrate is stirred vigorously with 5.06 g. (0.075 M) of methylamine hydrochloride, 10.5 ml. (0.075 M) of triethylamine and 10 ml. of water. After 12 hours, the solvent is distilled off and the residue is dissolved in ethyl acetate. The ethyl acetate layer is washed with 5% NaHCO$_3$ and 1N-HCl, followed by drying. The ethyl acetate is distilled off and the oily residue is treated with petroleum benzin. The crude crystals thus obtained are recrystallized from ethyl acetate-petroleum benzin. Yield 8.2 g. (63.3%); melting point: 48.0°–49.0° C; optical rotation $[\alpha]_D^{21} - 28.1°$ (c=0.68, in DMF).

Elemental analysis, for $C_{14}H_{18}O_3N_2$ - Calcd. C, 64.10; H, 6.92; N, 10.68; Found C, 64.03; H, 6.92; N, 10.65.

(b) Synthesis of BOC.His.Pro.NH.CH$_3$ 5.2 g. (0.02 M) of Z.Pro.NH.CH$_3$ is catalytically reduced in a conventional manner to H.Pro.NH.CH$_3$. Separately, 11.8 g. (0.02 M) of BOC.His (Tos).OH.D-CHA salt is suspended in ethyl acetate and vigorously shaken with 110 ml. of ice-cooled 0.2N-H$_2$SO$_4$. The ethyl acetate layer is washed twice with water and, after drying, the ethyl acetate is distilled off under reduced pressure. The oily residue and the H.Pro.NH.CH$_3$ prepared above are dissolved together in 200 ml. of a mixture of acetonitrile and methylene chloride (1:1), followed by ice-cooling. To this solution is added 4.12 g. (0.02 M) of DCC and the mixture is stirred for 12 hours. The byproduct dicyclohexylurea is filtered off and the filtrate is concentrated under reduced pressure. The oily residue is dissolved in 20 ml. of N,N-dimethylformamide, followed by addition of 2.70 g. (0.04 M) of Hobt. The mixture is allowed to stand at room temperature for 5 hours. The solvent is distilled off in vacuo and the residue is dissolved in ethyl acetate. The ethyl acetate layer is extracted three times with water. The water layer is adjusted to pH 8 with NaHCO$_3$, saturated with sodium chloride and extracted with ethyl acetate. The ethyl acetate layer is washed twice with a saturated aqueous solution of sodium chloride and dried over anhydrous Na$_2$SO$_4$. The ethyl acetate is distilled off under reduced pressure and the oily residue is treated with petroleum benzin. The resultant powder is recovered by filtration. Yield 2.60 g. (35.6%); melting point: 75.0°–80.0° C; optical rotation $[\alpha]_D^{21} - 22.7°$ (c=0.74; in N,N-dimethylformamide).

Elemental analysis, for $C_{17}H_{27}O_4N_5$ - Calcd. C, 55,87; H, 7.45; N, 19.17; Found C, 56.16; H, 7.55; N, 18.39.

(c) Synthesis of Oct.His.Pro.NH CH$_3$

In 15 ml. of 25% HBr/acetic acid is dissolved 1.46 g. (0.004 M) of BOC-His-Pro-NH-CH$_3$ and the solution is allowed to stand at room temperature for 20 minutes. Following addition of 150 ml of ether, the resultant precipitate is recovered by filtration and dried in a desiccator with NaOH for 12 hours. The dry powder thus obtained is dissolved in 15 ml. of N,N-dimethylformamide and, under cooling, 1.12 ml. (0.008 M) of triethylamine is added. The resultant salt is filtered off and the filtrate is used as it is for the next reaction. Separately, 645mg. (0.004 M) of 3-oxo-5-carboxyperhydro-1,4-thiazine and 720 mg. (0.004 M) of HONB are dissolved in 5 ml. of N,N-dimethylformamide and, under cooling, 825 mg. (0.004 M) of DCC is added. The mixture is stirred for 3 hours.

To this solution is added the amine solution previously prepared as above and the mixture is stirred at 4° C for 12 hours. The byproduct dicyclohexylurea is filtered off and the filtrate is concentrated in vacuo.

The residue is treated with ether to obtain a powder which is then dissolved in 100 ml. of a mixture of methanol and chloroform (1:9). The solution is run onto a column (5.0 × 12.0 cm) of silica gel. After the column is washed with 500 ml. of the same solvent, elution is carried out with a mixture of methanol and chloroform (4:6). The fractions rich in the contemplated compound are pooled and concentrated to remove the solvent. The residue is dissolved in a small amount of 0.1N-acetic acid and further purified by passage through a column (5.5 × 40.0 cm) of Sephadex LH-20. The fractions rich in the desired compound are pooled and lyophilized. Yield 1.04 g; optical rotation $[\alpha]_D^{21} - 62.6°$ (c=0.63, in H$_2$O); thin-layer chromatography — $Rf_1 = 0.36$.

Elemental analysis, for $C_{17}H_{24}O_4N_6S \cdot CH_3COOH \cdot 4H_2O$ - Calcd. C, 42.21; H, 6.71; N, 15.55; S, 5.93; Found C, 41.88; H, 5.20; N, 15.63; S, 6.42.

EXAMPLE 4

Synthesis of Oct.His.Pro.NHCH$_2$CH$_2$CH$_2$CH$_3$ (a) Synthesis of Z-Pro-NHCH$_2$CH$_2$CH$_2$CH$_3$ 12.5 g. (0.05 M) of Z-Pro-OH is converted to active ester as in Example 3 (a) and, with the addition of 5.7 ml. (0.06 M) of n-butylamine, it is stirred for 12 hours.

The dioxane is distilled off under reduced pressure and the residue is dissolved in ethyl acetate. The ethyl acetate layer is washed with 5% NaHCO$_3$ and 1N-HCl, followed by drying. The ethyl acetate is distilled off under reduced pressure and, following the addition of petroleum benzin, the residue is filtered. The crude product is recrystallized from ethyl acetate. Yield 14.0 g. (92.7%); melting point: 94.0°–95.0° C, optical rotation $[\alpha]_D^{21} - 39.6°$ (c=0.54, in N,N-dimethylformamide)

Elemental analysis for $C_{17}H_{24}O_3N_2$ - Calcd. C, 67.08; H, 7.95; N, 9.20; Found C, 66.83; H, 7.90; N, 9.05.

(b) Synthesis of BOC.His.Pro.NHCH$_2$CH$_2$CH$_2$CH$_3$

Using 6.1 g. (0.002 M) of Z.Pro-NHCH$_2$CH$_2$CH$_2$CH$_3$, the title compound is synthesized in the same manner as described in Example 3(b) for the synthesis of the methyl-compound. Yield 4.4 g. (53.5%), melting 65.0°–70.0° C, optical rotation $[\alpha]_D^{21} - 27.3°$ (c=0.70, in N,N-dimethylformamide).

Elemental analysis, for $C_{20}H_{33}O_4N_5$ - Calcd. C, 58.94; H, 8.16; N, 17.19; Found C, 59.05; H, 8.51; N, 16.47.

(c) Synthesis of Oct-His-Pro-NHCH$_2$CH$_2$CH$_2$CH$_3$

Using 1.63 g. (0.004 M) of BOC-His-Pro-NHCH$_2$CH$_2$CH$_2$CH$_3$, the title compound is synthesized in the same manner as described in Example 3 (c) for the synthesis of the methyl-compound. Yield 1.16 g.; optical rotation $[\alpha]_D^{21} - 65.0°$ (c=0.60, in water); thin-layer chromatography Rf$_1$=0.62.

Elemental analysis, for $C_{20}H_{30}O_4N_6S \cdot CH_3COOH \cdot 4H_2O$ - Calcd. C, 45.35; H, 7.25; N, 14.42; S, 5.50; Found C, 44.85; H, 5.75; N, 14.94; S, 6.36.

EXAMPLE 5

Synthesis of Oct-His-Pro-NHCH$_2$CH$_2$C$_6$H$_5$ (a) Synthesis of Z.Pro-NHCH$_2$CH$_2$C$_6$H$_5$ Using 12.5 g. (0.05 M) of Z.Pro.OH, the above compound is synthesized in the same manner as described in Example 4 (a) for the n-butyl compound. Yield 16.0 g. (90.9%); melting point: 86.0°–88.0° C; optical rotation $[\alpha]_D^{21} - 39.6°$ (c=0.54; in N,N-dimethylformamide)

Elemental analysis, for $C_{21}H_{24}O_3N_2$ - Calcd. C, 71.57; H, 6.86; N, 7.59; Found C, 71.38; H, 6.72; N, 7.87.

(b) Synthesis of BOC.His-Pro.NHCH$_2$CH$_2$C$_6$H$_5$

Using 7.0 g. (0.02 M) of Z.Pro.NHCH$_2$CH$_2$C$_6$H$_5$, the above compound is synthesized in the same manner as described in Example 3 (a) for the production of the methyl-compound. Yield 6.5 g. (71.4%); melting point: 70.0°–75.0° C (decomp.); optical rotation $[\alpha]_D^{21} - 21.7°$ (c=0.75, in N,N-dimethyl formamide) Elemental analysis, for $C_{24}H_{33}O_4N_5$-

Calcd. C, 63.27; H, 7.30; N, 15.38; Found C, 63.41; H, 7.49; N, 14.59.

(c) Synthesis of Oct-His-Pro-NHCH$_2$CH$_2$C$_6$H$_5$

Using 1.82 g (0.004 M) of BOC.His.-Pro.NHCH$_2$CH$_2$C$_6$H$_5$, the above compound is synthesized in the same manner as described in Example 3 (c) for the synthesis of the methyl-compound. Yield 1.37 g.; optical rotation $[\alpha]_D^{21} - 80.5°$ (c=0.56, in water); thin-layer chromatography Rf$_1$=0.64.

Elemental analysis, for $C_{24}H_{30}O_4N_6S \cdot CH_3COOH \cdot 3H_2O$ - Calcd. C, 52.52; H, 6.43; N, 14.13; S, 5.39; Found C, 52.15; H, 5.73; N, 14.32; S, 5.61.

EXAMPLE 6

Synthesis of Cbl His-Pro.NH$_2$ (a) Synthesis of γ-carboxy-γ-butyrolactone

In 200 ml. of water is suspended 29.4 g. (0.2 M) of H.Glu.OH, and a solution of 16.8 g. (0.24 M) of sodium nitrite in 120 ml. of water and 120 ml. of 2N-H$_2$SO$_4$ are simultaneously added dropwise at room temperature over a period of about 90 minutes. The reaction mixture is allowed to stand for 12 hours. The water is distilled off under reduced pressure and hot acetone is added to the residue. The acetone is distilled off from the extract and the oily residue is purified by distillation under reduced pressure. The desired compound is obtained as a distillate between 170.0 and 175.0° C/O 5 mmHg. Yield 14.3 g. (55.0%); melting point: 50° C; optical rotation $[\alpha]_D^{27} - 11.4°$ (c=0.77, in 2N-NaOH).

Elemental analysis, for $C_5H_6O_4 \cdot 1/2H_2O$ - Calcd. C, 44.61; H, 4.87; N, 0.00; Found C, 44.69; H, 4.77; N, 0.00.

(b) Synthesis of Cbl.His-Pro.NH$_2$ 1.43 g. (0.011 M) of γ-carboxy-γ-butyrolactone and 3.46 g. (0.013 M) of pentachlorophenol are dissolved in N,N-dimethylformamide and the solution is cooled with ice. Then, with the addition of 2.37 g. (0.0115 M) of DCC is added, the solution is stirred for 4 hours. Separately, 3.85 g. (0.01 M) of Z.His-Pro.NH$_2$ is treated as in Example 1(c) to obtain a solution of H.His-Pro.NH$_2$ in N,N-dimethylformamide. The above two solutions are combined and stirred at 4° C for 48 hours. The byproduct dicyclohexylurea is filtered off and the solvent is distilled off in vacuo. The residue is triturated with ethyl acetate and the resultant powder is recovered by filtration. The powder is washed twice with hot acetonitrile and, then, with ethyl acetate. The resultant powder is dissolved in water and the insoluble material is filtered off. The filtrate is freeze-dried. Yield 3.80 g.; optical rotation $[\alpha]_D^{22} - 53.4°$ (c=0.56, in water); thin-layer chromatography Rf$_1$=0.43.

Elemental analysis, for $C_{16}H_{21}O_5N_5 \cdot 5.5 H_2O$ - Calcd. C, 41.56; H, 7.17; N, 15.15; Found C, 41.55; H, 5.41; N, 15.02.

EXAMPLE 7

Synthesis of Cbl.His.Pip.NH$_2$ 390 mg. (0.003 M) of γ-carboxy-γ-butyrolactone is treated in the same manner as in Example 6 (b) to obtain the pentachlorophenyl ester.

Separately, 1.20 g. (0.003 M) of Z.His.Pip.NH$_2$ is treated in the same manner as that in Example 2 (c) to prepare a solution of H.His-Pip.NH$_2$ in N,N-dimethylformamide. The two solutions are combined and the mixture is stirred at 4° C for 12 hours. The byproduct dicyclohexylurea is filtered off and the filtrate is distilled under reduced pressure. The residue is triturated with ethyl acetate and the resultant powder is washed twice with hot acetonitrile and dissolved in 0.1N-acetic acid. The insoluble material is filtered off and the filtrate is purified by passage through a column (5.5 × 40.0 cm) of of Sephadex LH-20. The fractions rich in the desired compound are pooled and lyophilized. Yield 400 mg. optical rotation: $[\alpha]_D^{21} - 49.1°$ (c=0.86, in H$_2$O) thin-layer chromatography: Rf$_1$=0.45

Elemental analysis, for $C_{17}H_{23}O_5N_5 \cdot 1/2CH_3COOH \cdot 3H_2O$ - Calcd. C, 46.85; H, 6.77; N, 15.18; Found C, 46.62; H, 5.68; N, 15.35.

EXAMPLE 8

Synthesis of Cbl-His-Pro-NH-CH$_3$

By the procedure described in Example 6(b), 520 mg. (0.004 M) of γ-carboxy-γ-butyrolactone is converted to the pentachlorophenyl ester. Separately, 1.46 g. (0.004 M) of BOC-His-Pro-NH-CH$_3$ is treated by the procedure described in Example 3 (c) to prepare a solution of H-His-Pro-NH-CH$_3$ in N,N-dimethylformamide.

The two solutions are pooled and stirred at 4° C for 12 hours. The byproduct dicyclohexylurea is filtered off and the filtrate is distilled in vacuo. The residue is triturated with ethyl acetate. The resultant powder is re-precipitated twice from acetonitrile and ethyl acetate and dissolved in a small amount of 0.1N-acetic acid. The insolubles are filtered off. The filtrate is purified by passage through a column (5.5 × 40.0 cm) of Sephadex LH-20. The dominant fractions are pooled and lyophilized. Yield 860 mg.; optical rotation; $[\alpha]_D^{21} - 68.0°$ (c=0.63; in H$_2$O); thin-layer chromatography Rf$_1$=0.35.

Elemental analysis, for C$_{17}$H$_{23}$O$_5$N$_5$.1/2CH$_3$COOH.3H$_2$O - Calcd. C, 46.85; H, 6.77; N, 15.18; Found C, 46.88; H, 5.79; N, 15.17.

EXAMPLE 9

Synthesis of Cbl.His-Pro-NHCH$_2$CH$_2$CH$_2$CH$_3$

Using 520 mg. (0.004 M) of γ-carboxy-γ-butyrolactone and 1.63 g. (0.004 M) of BOC-His-Pro-NHCH$_2$CH$_2$CH$_2$CH$_3$, the above compound is synthesized in the same manner as set forth in Example 8 for the methyl-compound. Yield 852 mg.; optical rotation $[\alpha]_D^{21} - 66.4°$ (c=0.67, in H$_2$O) thin-layer chromatography: Rf$_1$=0.60

Elemental analysis, for C$_{20}$H$_{29}$O$_5$N$_5$.1/2CH$_3$COOH.3.5 H$_2$O - Calcd. C, 49.21; H, 7.47; N, 13.67; Found C, 48.85; H, 6.40; N, 13.80.

EXAMPLE 10

Synthesis of Cbl-His-Pro-NHCH$_2$CH$_2$C$_6$H$_5$

Using 520 mg. (0.004 M) of γ-carboxy-γ-butyrolactone and 1.82 g. (0.004 M) of BOC-His-Pro-NHCH$_2$CH$_2$C$_6$H$_5$, the above compound is synthesized in the same manner as Example 8 for the synthesis of the methyl-compound. Yield 517 mg. optical rotation $[\alpha]_D^{21} - 78.8°$ (c=0.52, in H$_2$O) thin-layer chromatography: Rf$_1$=0.63

Elemental analysis, for C$_{24}$H$_{29}$O$_5$N$_5$.1/2CH$_3$COOH.6H$_2$O Calcd. C, 49.58; H, 7.16; N, 11.57; Found C, 49.63; H, 5.43; N, 11.96.

EXAMPLE 11

Synthesis of Oct-His-Pro-NHCH$_2$CH$_2$CH$_2$CH$_2$CH$_3$ (a) Synthesis of Z-His-Pro-O$^t$Bu Z-Pro-O$^t$Bu 10.0 g. (0.033 M) in methanol is hydrogenated over a Pd catalyst. The catalyst is removed by filtration and the filtrate is condensed under reduced pressure. To the residue is added a cold solution of Z-His-N$_3$ [prepared from Z-His-NHNH$_2$ 9.1 g. (0.03 M)] in ethylacetate. The mixture is stirred at 4° C for 72 hours and then washed with a 5% aqueous solution of sodium bicarbonate and water. The solvent is evaporated under reduced pressure. The residue is triturated with petroleum-ether and recrystallized from ethylacetate. Yield 9.5 g. (71.4%); melting point: 143°–145° C; optical rotation $[\alpha]_D^{26} - 41.7°$ (c=0.47, in DMF).

Elemental analysis, for C$_{23}$H$_{30}$O$_5$N$_4$ - Calcd. C, 62.42; H, 6.83; N, 12.66; Found C, 62.15; H, 6.75; N, 12.71.

(b) Synthesis of Oct-His-Pro-OH

DCC 2.06 g. (0.01 M) is added to a solution of H-His-Pro-O$^t$Bu prepared from Z-His-Pro-O$^t$Bu 4.42 g. (0.01 M) by catalytic hydrogenation, 3-oxo-5-carboxyperhydro-1,4-thiazine 1.61 g. (0.01 M) and HONB 1.79 g. (0.01 M) in DMF and the mixture is stirred at room temperature for 12 hours. The urea formed is filtered off and the filtrate is evaporated in vacuo. The residue is triturated with ether, then collected by filtration and dried over P$_2$O$_5$ in vacuo. The dried powder is treated with 25 ml. of trifluoroacetic acid at room temperature for 3 hours to remove the t-butyl ester. The excess of acid is evaporated under reduced pressure and the residue is triturated with ether, then collected by filtration and dried over NaOH pellets in vacuo.

The dried powder is dissolved in a mixture of chloroform-methanol (9:1) and charged on the top of a silica-gel column (5.0 × 8.0 cm). The column is washed with the same solvent and then eluted with a mixture of chloroform-methanol (6:4). The main fractions are collected and concentrated under reduced pressure. The residue is dissolved in 50 ml. of 0.2N-HCl under ice-cooling and then lyophilized. Yield 2.60 g. (60.5%); optical rotation $[\alpha]_D^{21} - 61.9°$ (c=0.49, in water); thin-layer chromatography Rf$_1$=0.35.

Elemental analysis, for C$_{16}$H$_{21}$O$_5$N$_5$S.HCl.2.5H$_2$O - Calcd. C, 40.29; H, 5.72; N, 14.68; S, 6.23; Found C, 40.28; H, 5.09; N, 14.65; S, 6.19.

(c) Synthesis of Oct-His-Pro-NHCH$_2$CH$_2$CH$_2$CH$_2$CH$_3$

DCC 620 mg. (0.003 M) is added to a mixture of Oct-His-Pro-OH 432 mg. (0.001 M), HONB 269 mg. (0.0015 M) and n-amylamine 0.29 ml. (0.0025 M) in DMF and the mixture is stirred at room temperature for 48 hours. The urea formed is filtered off and the filtrate is evaporated in vacuo. The residue is triturated with ether and the resulting powder is purified in the same manner as described in Example 3 (c). Yield 110 mg.; optical rotation $[\alpha]_D^{21} - 65.4°$ (c=0.35, in water); thin-layer chromatography Rf$_1$=0.73.

Elemental analysis, for C$_{21}$H$_{32}$O$_4$N$_6$S.CH$_3$COOH.2H$_2$O - Calcd. C, 49.27; H, 7.19; N, 14.99; S, 5.72; Found C, 48.83; H, 6.56; N, 15.36; S, 5.57.

EXAMPLE 12

The compounds listed below are prepared in the same manner as described in Example 11 (c) by using the corresponding amines.

Synthesis of Oct-His-Pro-NHCH$_2$CH$_3$

Yield 137 mg.; optical rotation $[\alpha]_D^{21} - 67.7°$ (c=0.31, in water); thin-layer chromatography Rf$_1$=0.55;

Elemental analysis, for C$_{18}$H$_{26}$O$_4$N$_6$S.CH$_3$COOH.H$_2$O - Calcd. C, 47.99; H, 6.44; N, 16.79; S, 6.41; Found C, 47.74; H, 6.43; N, 16.74; S, 6.15.

Synthesis of Oct-His-Pro-NH-CH$_2$CH$_2$CH$_3$

Yield 90 mg.; optical totation $[\alpha]_D^{21} - 51.6°$ (c=0.31, in water); thin-layer chromatography Rf$_1$=0.65

Elemental analysis, for $C_{19}H_{28}O_4N_6S \cdot CH_3COOH \cdot 2H_2O$ - Calcd. C, 47.36; H, 6.81; N, 15.78; S, 6.02; Found C, 47.29; H, 6.13; N, 15.49; S, 6.02.

Synthesis of Oct-His-Pro-NHCH$_2$CH$_2$CH$_2$CH$_2$CH$_2$C$_3$

Yield 105 mg.; optical rotation $[\alpha]_D^{23} -66.4°$ (c=0.54, in water); thin-layer chromatography Rf$_1$=0.70

Elemental analysis, for $C_{22}H_{34}O_4N_6S \cdot CH_3COOH \cdot 2H_2O$ - Calcd. C, 50.16; H, 7.36; N, 14.62; S, 5.58; Found C, 49.76; H, 7.18; N, 15.78; S, 5.66.

By the same procedure as above, the following peptides can be produced.

Oct-His-Pro-NHCH$_2$CH$_2$OCH$_3$,
Cbl-His-Pro-NHCH$_2$CH$_2$OCH$_3$,
Oct-His-Pro-NHCH$_2$CH$_2$OH,
Cbl-His-Pro-NHCH$_2$CH$_2$OH,
Oct-His-Tac-NH$_2$,
Oct-His-Tac-NHCH$_2$CH$_2$CH$_2$CH$_3$,
Oct-His-Tac-NHCH$_2$CH$_2$OCH$_3$,
Oct-His-Tac-NHCH$_2$CH$_2$OH,
Cbl-His-Tac-NH$_2$,
Cbl-His-Tac-NHCH$_2$CH$_2$CH$_2$CH$_3$,
Cbl-His-Tac-NHCH$_2$CH$_2$OCH$_3$,
Cbl-His-Tac-NHCH$_2$CH$_2$OH,

Pharmacological Test Results

Test procedure (1) TSH-releasing activity

Using rats, a test was performed in accordance with the method of Schally et al. [J. Biol. Chem. 244, 4077, (1969)].

(2) Anaesthesia antagonism (anti-depressant activity)

55 mg/kg of pentobarbital sodium was intraperitoneally given to mice (ICR/JCL, male, 4 weeks old) and, when the righting reflex had disappeared, namely after 10 minutes, the compound (I) and TRH (physiological saline for control) were intravenously administered and the times which had elapsed before a recovery of the righting reflex took place [Prange et al, Life Sci 14, 447-55, (1974)].

(3) Activity-increasing action

Using groups of 10 mice (ICR/JCL, male, 4 weeks old), each mouse was placed in an activity wheel and the activity-increasing action of the medication on the mouse was observed. The cumulative number of rotations caused by the spontaneous activity of the mice during a period of 3 hours following the intravenous administration of compound (I) was compared with the number of revolutions for the control group.

(4) Dopamine activity-potentiating effect

Using groups of 10 male mice (ICR/JCL) with one of its caudate nuclei destroyed by suction the effects of compound (I) upon the number of turns and the percent incidence of head turning as caused by 0.25 mg/kg of apomorphine (I.P.), i.e., a dopamine-receptor stimulant, under the influence of premedication (18–22 hours) with 2 mg/kg of reserpine (i.p.) were examined.

Thus, compound (I) was given 30 minutes before the administration of apomorphine and the result was compared with that for the untreated (control group). This test was performed to ascertain the potentiating effect of the compound upon the central nervous system action of dopamine, the principle of the test being the same as that of the experiment performed by Everett et al. [Fed. Proc. 23, 198, (1964)] for testing the DOPA synergistic effect which involved the administration of Dl-DOPA.

The relative effects of compound (I) by the above 4 procedures were expressed in terms of the ratios of effect of the same dose of compound (I) as that of TRH with the effects of TRH being taken as unity. The results are summarized in the following table.

Table 1

| Compound | TSH-releasing effect | Anaesthesia antagonism | Spontaneous activity-increasing effect | Dopamine-potentiating effect |
|---|---|---|---|---|
| TRH | 1 | 1 | 1 | 1 |
| Oct-His-Pip-NH$_2$ | 0.5 | 1.57 | 5 | 4.00 |
| Cbl-His-Pro-NH$_2$ | 0.01–0.02 | 1.25 | 1.0 | 16.00 |

The compounds (I) according to this invention can be produced by the same method as described in the foregoing examples and tested for their pharmacological effects by the same testing procedures as hereinbefore described.

What is claimed is:

1. A member selected from the group consisting of a compound of the formula

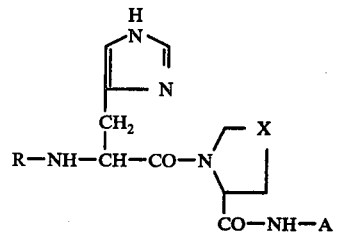

wherein A represents hydrogen, alkyl of up to 10 carbon atoms, aralkyl of up to 10 carbon atoms, alkoxyalkyl of up to 9 carbon atoms, hydroxyalkyl of up to 9 carbon atoms or alkoxy of up to 9 carbon atoms, R represents

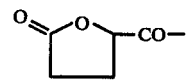

X represents —S— or —(CH$_2$)$_n$— wherein n is 1 or 2, and a pharmacologically acceptable acid salt thereof.

2. A compound according to claim 1 wherein R and other constituent amino acid residues are all of the L-configuration.

3. A compound according to claim 1 wherein the compound is L-2-oxo-tetrahydrofuran-5-carbonyl-L-histidyl-L-prolinamide.

* * * * *